US00PP10555P

United States Patent [19]

Bjorge et al.

[11] Patent Number: Plant 10,555

[45] Date of Patent: Aug. 18, 1998

[54] 'FA 12' PEACH TREE

[75] Inventors: Annette Bjorge; Randy Bjorge, both of Coloma, Mich.

[73] Assignee: International Plant Management, Lawrence, Mich.

[21] Appl. No.: 738,252

[22] Filed: Oct. 28, 1996

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new peach variety, *Prunus persica*, (hereinafter referred to as the 'FA 12' peach tree) which was developed by Annette and Randy Bjorge in a breeding program at Fruit Acres Farm in Coloma, Mich., having the following combination of unique and desirable features:

1. A substantially round fruit with an attractive bright red blush coloration covering 90 to 100% of the fruit at maturity. pg.2
2. A fruit maturing 5 days later than the 'Redhaven' peach.
3. A fruit with excellent storage and shipping qualities.
4. A tree and fruit with good resistance to bacterial spot.
5. A fruit with flesh that does not brown when cut.
6. A fruit and blossom that is very hardy.

3 Drawing Sheets

ORIGIN OF THE VARIETY

The new variety of peach tree 'FA 12' was developed by Annette and Randy Bjorge in a peach breeding program at Fruit Acres Farms, 2559 Friday Road, Coloma, Mich. 49038. The 'FA 12' peach tree was developed as a first generation cross between 'Fayette' and 'Newhaven', two established, non-patented, commercial varieties. The parent tree was grown and maintained in a peach tree breeding orchard in Fruit Acres Farms. This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of large, upright growth with medium density and is a regular and very productive bearer of peaches. The fruit of the new variety is characterized by its round, substantially 90 to 100% bright red blushed, fruits that present a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The tree and fruits of the new variety exhibit good resistance to Bacterial Spot. The fruit matures in the beginning of the peach growing season in Southwestern Mich. It ripens 5 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

FIG. 1. illustrates specimens of the fully ripened fruit and foliage of the new variety.

FIG. 2. illustrates blooms of the new variety.

FIG. 3. Illustrates two specimens of the new variety. The lower specimen is bisected along the suture, the upper specimen is bisected as a ninety-degree angle to the plane of the suture. The color and forms of the flesh, pit and pit cavity are illustrated.

DETAILED DESCRIPTION OF THE VARIETY

Figure 1:
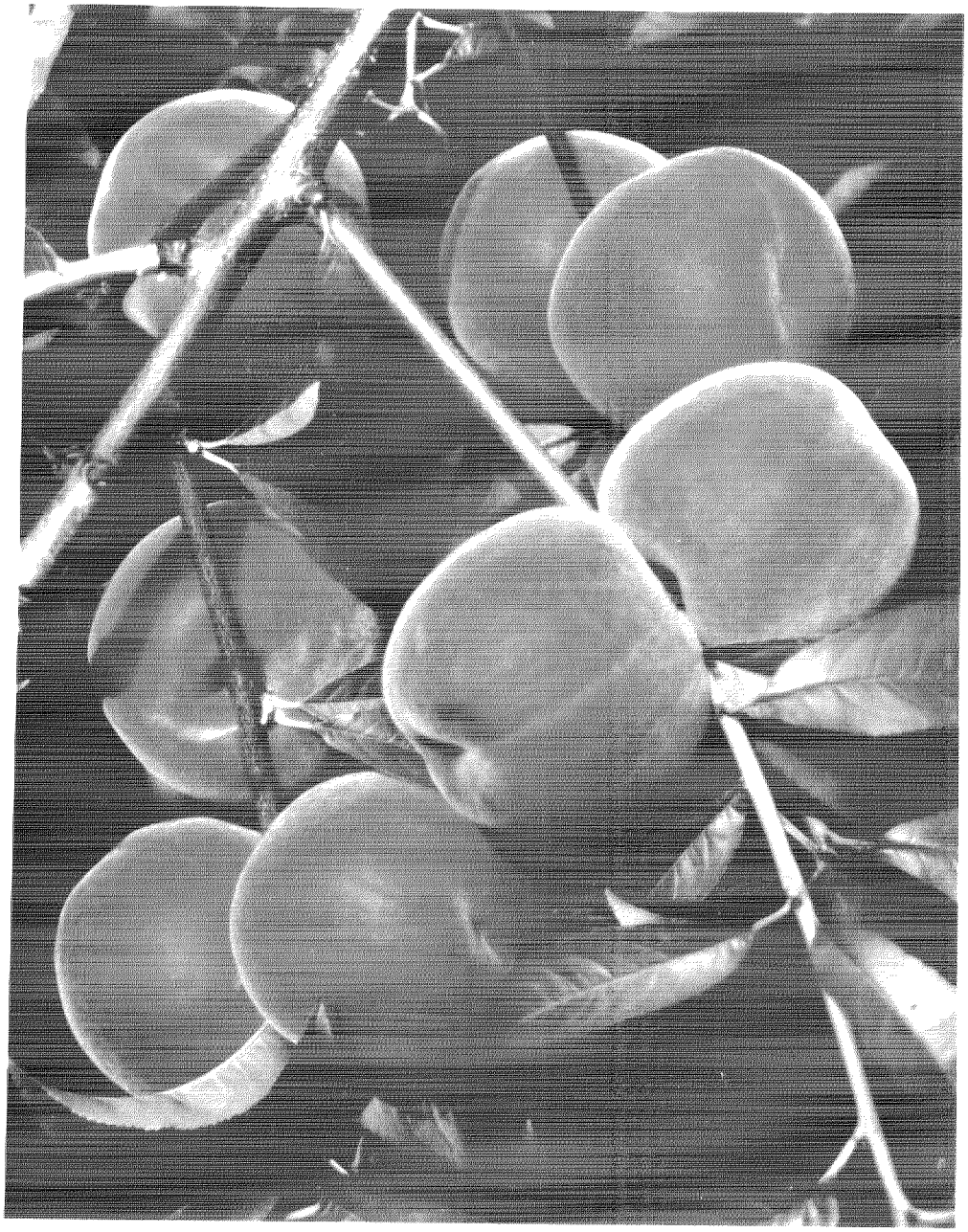
Figure 2:
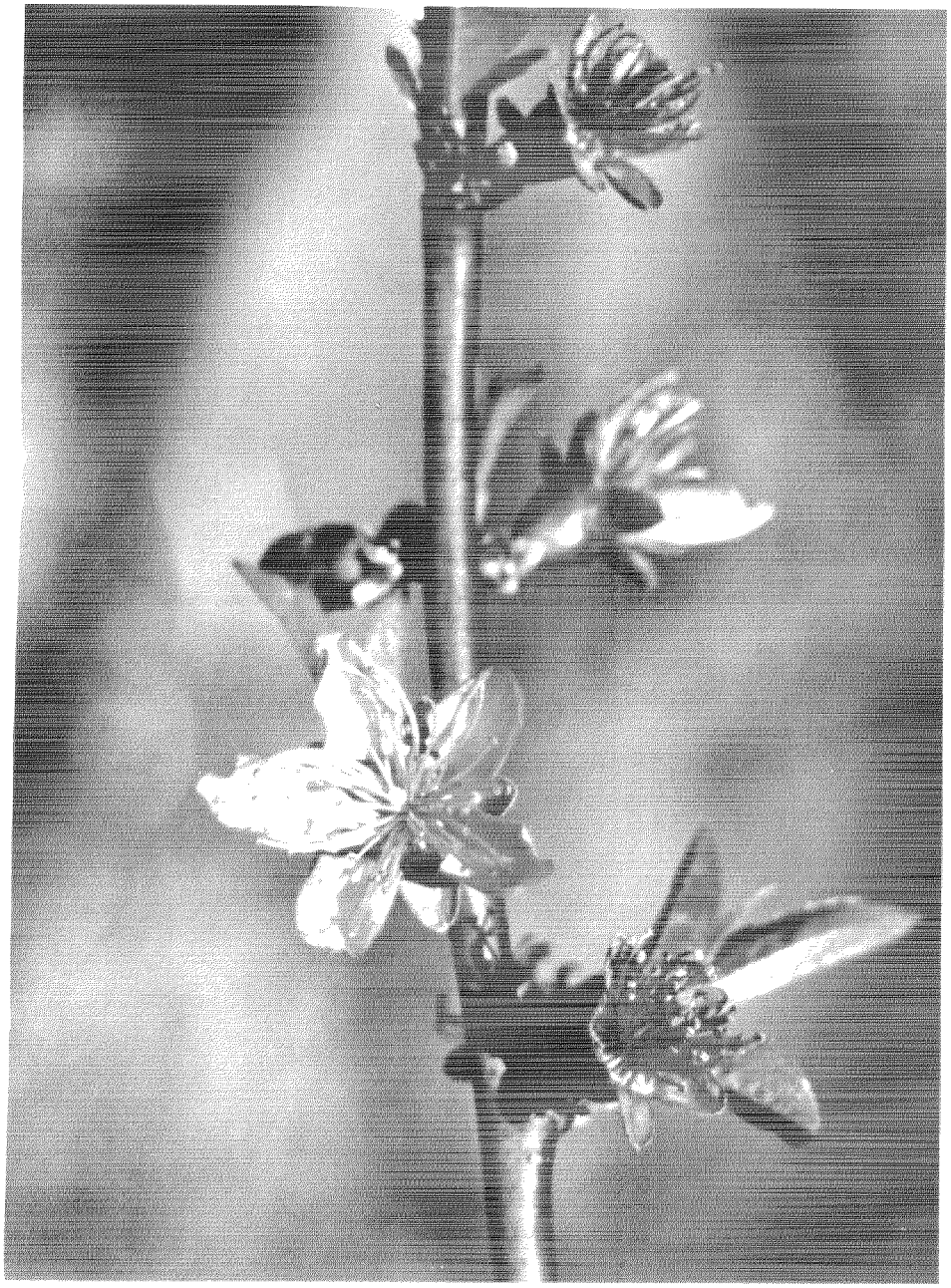
Figure 3:
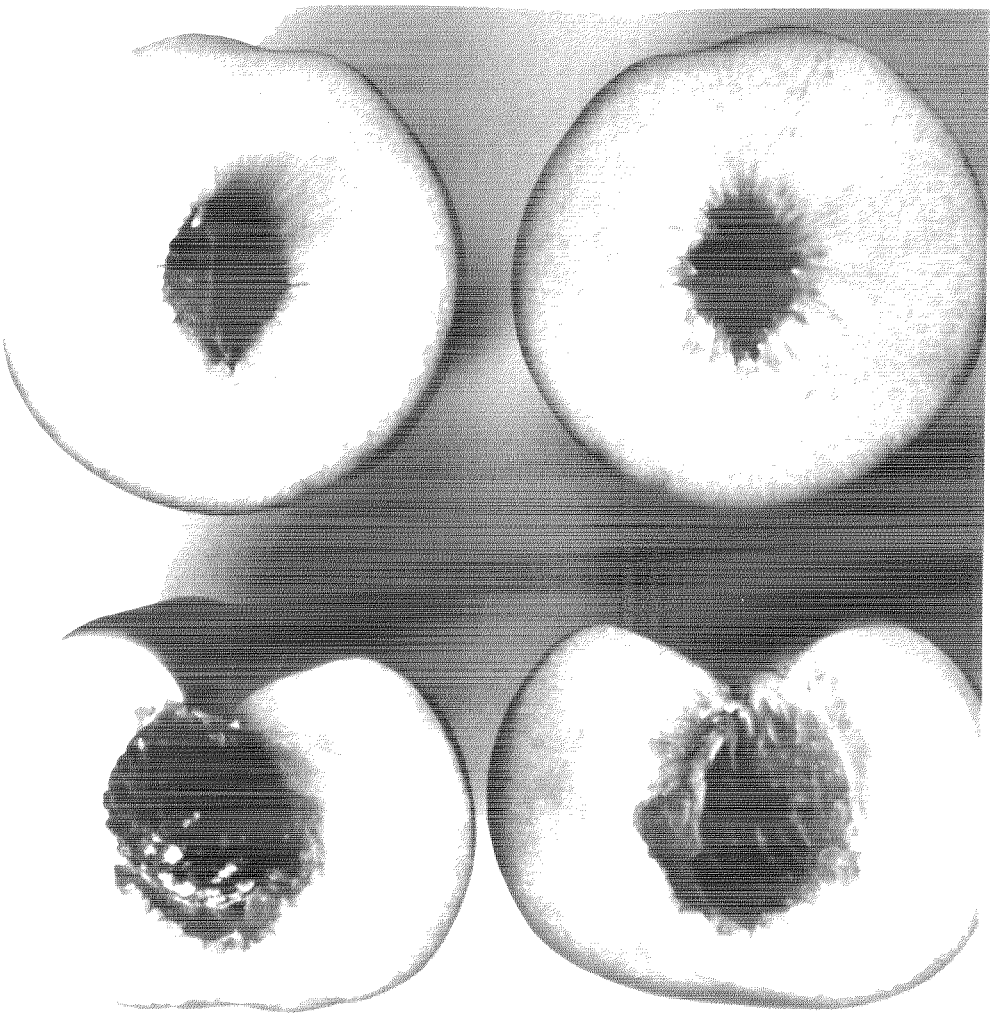

The following description of the fruit and foliage of the new variety is based on observation made in Berrien and Van Buren County of Southwestern Michigan. The color terminology is in accordance with The Royal Horticultural Society Colour Chart, published by The Royal Horticultural Society of London, England.

Tree:

*Age of specimen.*—7 years old.
*Height.*—Unpruned 4.9 M.
*Width.*—Unpruned 5.5 M
*Size.*—Medium-large.
*Vigor.*—High.
*Density.*—Open, internode distance is 1 to 2 cm.
*Form.*—Upright and spreading, major scaffold branches at a 50 to 60° angle, forms a central leader, does not require support.
*Production.*—Excellent, much more productive than its parents and 'Redhaven', ripens in 2 pickings with 60 % of the crop ripening for the first picking and 40% of the crop ripening for the second picking . Requires spring pruning but not summer pruning.
*Bearing.*—Annual, harvest season lasts 5 days in an average year, crop will hold 1 week on the tree and 4 weeks in common cold storage.
*Disease resistance.*—Good resistance to Bacterial Spot.
*Cold hardiness.*—Very hardy, hardier than parents and 'Redhaven'.

Trunk:

*Size.*—Medium small.
*Surface.*—Smooth.
*Lenticils.*—Small.
*Color.*—Gray 201 B.

Leaves:

*Size.*—Length 150 mm, width 41 mm, not including petiole.
*Form.*—Lanceolate, apex acute, base acute.

*Thickness.*—Medium.
*Texture.*—Medium.
*Margin.*—Crennate.
*Petiole.*—*Length* 8–10 mm, 1 mm thick.
*Glands.*—Globose, 2 to 4 on upper petiole and lower leaf blade.
*Color.*—Upper surface green 147 A, lower surface green 147 B.
*Stipules.*—None.

Flower buds:
*Size.*—Medium.
*Length.*—Medium.

Flowers:
*Blooming period.*—April 8 to April 15 in Coloma, Mich.
*Presentation.*—Medium showy.
*Pollen.*—Present, self-fertilizing.
*Petals.*—5 in number, cupped, 11 mm long, 9 mm wide, Red-Purple 73 A.
*Stamens.*—Slightly curved.
*Pistils.*—16 mm, White 155 A.

Fruit:
*Maturity when described.*—Firm ripe.
*Date of first picking.*—August 16 in southwestern Michigan, 5 days after 'Redhaven'.
*Date of last picking.*—August 21 in southwestern Michigan
*Size.*—68 to 80mm.
*Form.*—Round, slightly oblate, somewhat high shoulder.
*Suture.*—Inconspicuous.
*Pistil point.*—Recessed.

Skin:
*Thickness.*—Medium.
*Texture.*—Fine.
*Tendency to crack.*—None.
*Down.*—Moderate.
*Color.*—100% Red 46 A blush over orange-yellow 34 A.

Flesh:
*Texture.*—Firm, holds well for shipping, melting at maturity.
*Aroma.*—Excellent, very aromatic.
*Fibres.*—Few, small, tender, not conspicuous or noticeable in eating.
*Color.*—Yellow-orange 20 A.
*Coloration at pit.*—Very slight pinkish-red color bleeding into flesh around 30 to 40% of pit cavity.
*Eating quality.*—Best, very mild flavor with medium sweetness and acidity.

Stone:
*Size.*—Length 33 mm, width 25 mm, thickness 16 mm.
*Form.*—Ovate.
*Apex.*—Pointed.
*Sides.*—Equal.
*Base.*—Wide, slanted.
*Surface.*—Pitted to furrowed throughout.
*Color.*—Grayed orange 166 A.
*Type.*—Freestone.
*Tendency to crack.*—None.

Use: Desert, fresh and commercial market.
Shipping quality: Excellent.
Keeping quality: Excellent, 4 weeks in common cold storage.
Disease resistance:Good resistance to Bacterial Spot.

We claim:

1. A new and distinct variety of peach tree, *Prunus persica*, substantially as herein shown and described, characterized particularly as to novelty by the unique combination of large size, very vigorous, upright, very hardy, spreading, medium density, regular bearing tree, with good resistance to bacterial spot, producing freestone fruits having non-browning flesh and substantially round, firm, 90 to 100% blushed, bright red skin color at maturity which occurs 5 days after the maturity of 'Redhaven' peach.

* * * * *

FA 12